(12) United States Patent
Stenzler

(10) Patent No.: US 6,435,175 B1
(45) Date of Patent: Aug. 20, 2002

(54) PULMONARY DRUG DELIVERY DEVICE

(75) Inventor: Alex Stenzler, Orange, CA (US)

(73) Assignee: Sensormedics Corporation, Yorba Linda, CA (US)

( * ) Notice: Subject to any disclaimer, the term of this patent is extended or adjusted under 35 U.S.C. 154(b) by 71 days.

(21) Appl. No.: 09/650,491

(22) Filed: Aug. 29, 2000

(51) Int. Cl.[7] ............................................ A61M 11/00
(52) U.S. Cl. ......................... 128/200.14; 128/200.16; 128/202.25; 128/204.21
(58) Field of Search ..................... 128/200.14, 200.16, 128/200.22, 203.12, 204.21, 204.23, 202.25, 202.26

(56) References Cited

U.S. PATENT DOCUMENTS

| | | | | |
|---|---|---|---|---|
| 4,294,407 A | * | 10/1981 | Reichl et al. | 128/200.16 |
| 4,300,546 A | * | 11/1981 | Kruber | 128/200.16 |
| 4,334,531 A | * | 6/1982 | Reichl et al. | 128/200.16 |
| 4,801,086 A | | 1/1989 | Noakes | 239/3 |
| 4,877,989 A | * | 10/1989 | Drews et al. | 128/200.16 |
| 4,984,158 A | * | 1/1991 | Hillsman | 600/534 |
| 5,020,527 A | * | 6/1991 | Dessertine | 128/200.23 |
| 5,134,993 A | * | 8/1992 | Van Der Linden et al. | 128/200.23 |
| 5,167,506 A | * | 12/1992 | Killis et al. | 128/200.23 |
| 5,247,842 A | | 9/1993 | Kaufman et al. | 73/865.5 |
| 5,261,601 A | * | 11/1993 | Ross et al. | 128/200.16 |
| 5,280,784 A | * | 1/1994 | Kohler | 128/200.16 |
| 5,284,133 A | * | 2/1994 | Burns et al. | 128/200.23 |
| 5,333,106 A | * | 7/1994 | Lampher et al. | 128/200.23 |
| 5,363,842 A | * | 11/1994 | Mishelevich et al. | 128/200.23 |
| 5,392,768 A | * | 2/1995 | Johansson et al. | 128/204.23 |
| 5,404,871 A | * | 4/1995 | Goodman et al. | 128/204.23 |
| 5,452,711 A | * | 9/1995 | Gault | 128/200.16 |
| 5,487,378 A | * | 1/1996 | Robertson et al. | 128/204.23 |
| 5,551,416 A | * | 9/1996 | Stimpson et al. | 128/200.16 |
| 5,551,951 A | | 9/1996 | Fradkin | 601/115 |
| 5,688,232 A | | 11/1997 | Flower | 604/20 |
| 5,737,666 A | | 4/1998 | Lior et al. | 399/57 |
| 5,813,614 A | | 9/1998 | Coffee | 239/690 |
| 5,838,002 A | | 11/1998 | Sheehan | 250/288 |
| 5,875,776 A | | 3/1999 | Vaghefi | 128/203.15 |
| 5,935,099 A | | 8/1999 | Peterson et al. | 604/65 |
| 5,950,619 A | | 9/1999 | van der Linden et al. | 128/200.16 |
| 6,017,318 A | | 1/2000 | Gauthier et al. | 600/578 |
| 6,026,809 A | | 2/2000 | Abrams et al. | 128/203.15 |
| 6,070,761 A | | 6/2000 | Bloom et al. | 222/81 |

* cited by examiner

Primary Examiner—Aaron J. Lewis
(74) Attorney, Agent, or Firm—Lyon & Lyon LLP

(57) ABSTRACT

A nebulizer for delivering a drug to a patient includes an electronic control unit, a hand piece connected to the electronic control unit via a cable, and a cartridge detachably engaged with the hand piece. The electronic control unit includes a controller, a cartridge reader, a dosage storage element, and a display. The display preferably displays the drug name and the number of dosages remaining in the cartridge. The cartridge includes a head or nebulizer element for creating a fine mist or cloud of the drug in droplet form. The cartridge also includes a storage container containing a drug and a pump for pumping the drug to the nebulizer element. The cartridge also contains an information storage element for containing information regarding the drug and the drug delivery protocol for the patient. The information in the information storage element is transmitted to the electronic control unit when the cartridge is engaged with the hand piece.

29 Claims, 3 Drawing Sheets

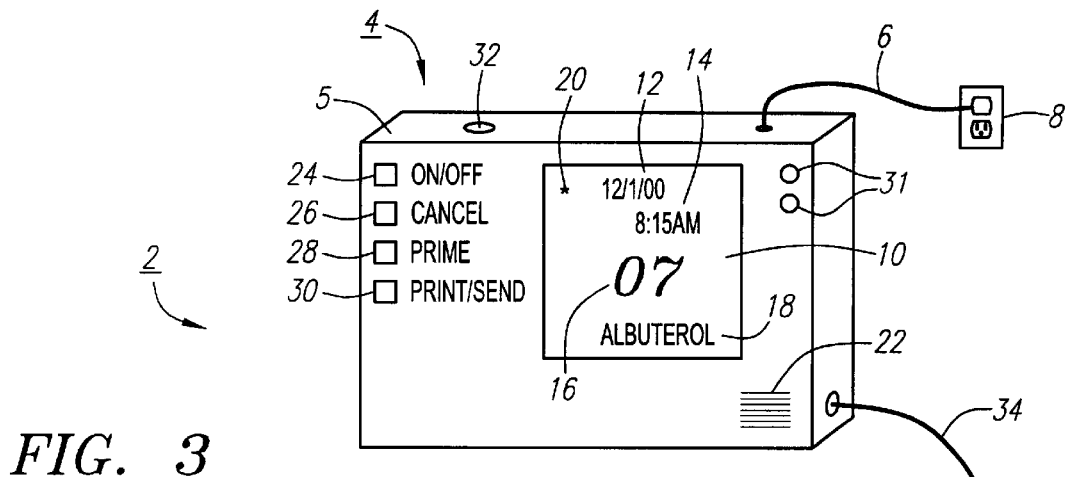
FIG. 3
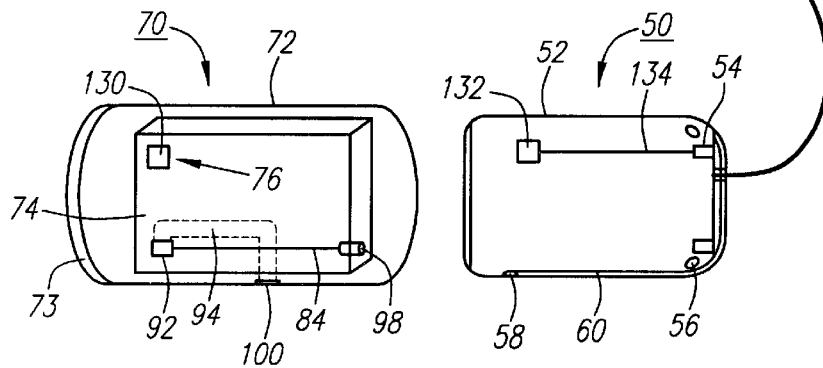
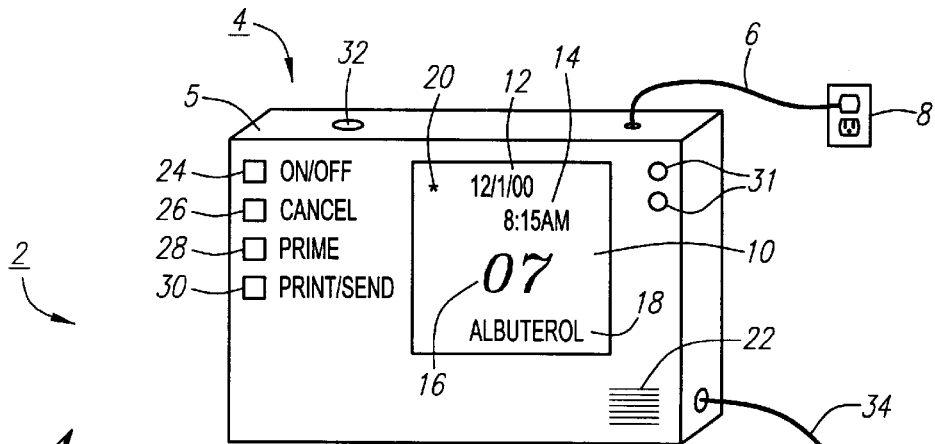
FIG. 4
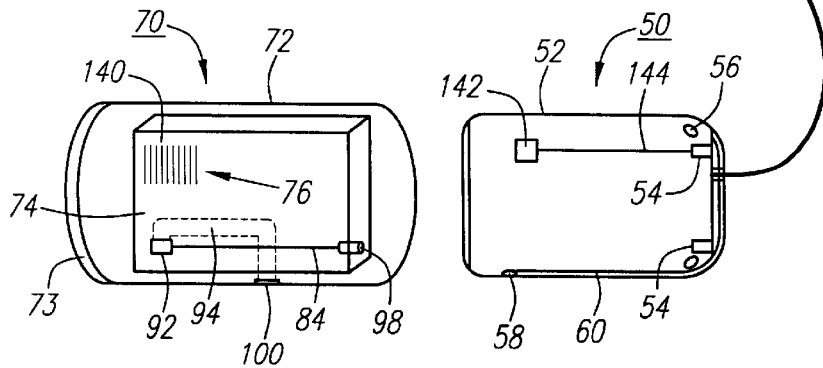

PULMONARY DRUG DELIVERY DEVICE

BACKGROUND OF THE INVENTION

The present invention relates generally to pulmonary drug delivery devices. More specifically, the invention relates to a nebulizer system for delivering a drug-containing aerosol to the lungs. The invention also relates to smart drug cartridges that contain information pertaining to the type of drug, the delivery protocol for the drug, and other patient specific information.

Drugs are increasingly being developed that are delivered to patients via inhalation. These drugs include various pharmaceutical compounds and mixtures directed to treat lung diseases such as asthma. Drugs that are directed to non-respiratory system diseases can also be delivered to the patient via inhalation. An example of this type of systemic drug is an inhaled form of insulin used to treat diabetes.

Most of these drugs require a precise unit dose delivery. If too little drug is given, the therapeutic effect of the drug can be reduced or lost entirely. If too much drug is delivered, the patient may suffer from toxic effects of the drug or may overdose.

Control of unit dose delivery is particularly hard for drugs delivered via inhalation. In the case of a nebulizer or inhaler-type devices, patients frequently forget if they took their medication. Even if a patient remembers that he or she took their medication, they might not know at what time their last inhalation was. This is problematic when a particular treatment or drug requires a specified time interval between successive doses.

Another difficulty that has arisen with respect to conventional inhalation devices relates to the preparation of the drugs. Sometimes one or more drugs are mixed with each other or a carrier prior to delivery. Albuterol, for example, typically requires that the drug (Albuterol) be mixed with a saline type solution. These mixtures can be prepared by the patient, or alternatively, by the patient's health care provider. Unfortunately, there may be mistakes made in preparing the final drug formulation.

Still another difficulty relates to mistakes made as to what drug is contained within a particular drug storage container. Consequently, the patient or health care provider might mistakenly administer the wrong drug. In yet another difficulty, the inhaled drug might have reached or exceeded the drug's expiration date. Unless the patient carefully reads the expiration label, there is a chance the patient is inhaling a drug that is expired. Another difficulty relates to patient compliance. Currently, drugs delivered via a nebulizer can take as long as ten to fifteen minutes to deliver the required dose. This long amount of time required to deliver each dose can reduce patient compliance.

Accordingly, there is a need for a device that can precisely control the unit dose delivery of an inhaled drug. The device can preferably monitor and assess various parameters such as when the last dose was delivered, the identification of the drug, the drug's expiration date, the concentration of the drug, the drug delivery protocol, etc. A device is needed that reduces the total time required to deliver an inhaled drug to a patient. Preferably, the device can be used at home. There also is a need for a drug cartridge that contains the drug as well as information relating to the drug and its intended delivery to the patient. Preferably, the information is stored in the drug cartridge and can be customized to a particular drug and/or patient.

SUMMARY OF THE INVENTION

In a first aspect of the invention, a nebulizer for delivering a drug to a patient includes an electronic control unit, a hand piece connected to the electronic control unit, and a cartridge that is detachably engaged with the hand piece. The cartridge includes a storage container for containing the drug. A pump is located on the cartridge and pumps the drug to a nebulizer element. The cartridge also includes an information storage element. The information storage element contains information on the drug contained within the cartridge as well as drug delivery protocol. When the cartridge is engaged with the hand piece, the information in the information storage element is transmitted to the electronic control unit. Information is displayed on a display on the electronic control unit.

In another aspect of the invention, the electronic control unit of the device includes a controller, a cartridge reader, and a dosage storage element. The cartridge reader reads the information contained within the information storage element on the cartridge. The dosage storage element countdowns the remaining doses of the cartridge. The number of remaining doses is displayed on the display.

In another aspect of the invention, the device includes data transmission means for transmitting patient compliance: information to an output device.

It is an object of the invention to create a nebulizer device that can read pre-programmed information stored within a cartridge containing a drug. The information relates to the type of drug contained with the cartridge and the individual delivery protocol for the patient. The information can be pre-programmed by the drug manufacturer or health care provider. The device preferably displays the remaining number of doses in the cartridge on a display. The device operates in accordance with pre-preprogrammed set of instructions stored within the information stored within the cartridge. It is also an object of the invention to have a device that can transmit patient compliance information to external to an output device.

In still another aspect of the invention, a cartridge for containing a drug includes a drug storage container for storing the drug, a pump disposed in the cartridge for pumping drug from the storage container to a conduit, and a programmable information storage element disposed in the cartridge.

BRIEF DESCRIPTION OF THE DRAWINGS

FIG. 3 illustrates the pulmonary delivery device according to another embodiment of the invention.

FIG. 4 illustrates the pulmonary delivery device according to another embodiment of the invention.

DETAILED DESCRIPTION OF THE PREFERRED EMBODIMENTS

Figure 1:
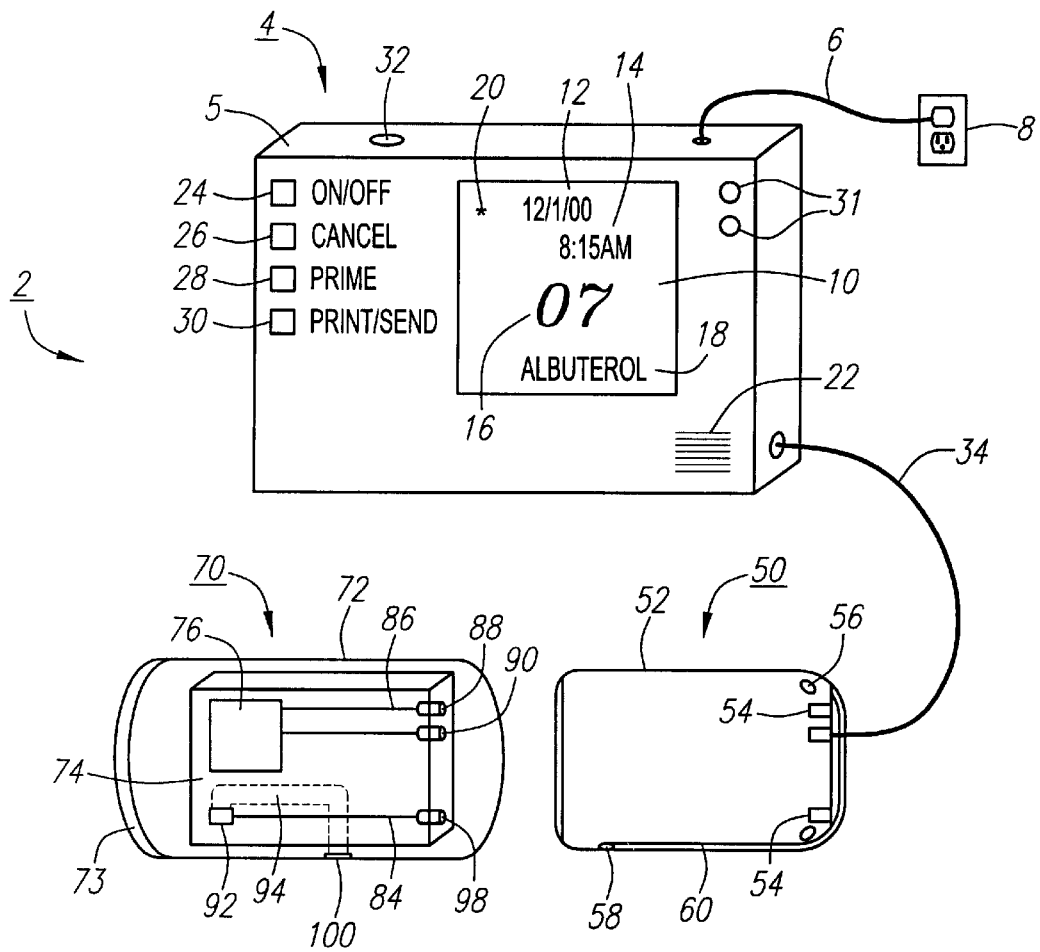
FIG. 1 illustrates the pulmonary delivery device according to one embodiment of the invention, including the electronic control unit, the hand piece, and the cartridge.

FIG. 1 illustrates the pulmonary drug delivery device 2. The device 2 generally comprises an electronic control unit 4, a hand piece 50, and a cartridge 70. The electronic control unit 4 includes a housing 5 and receives power via a power cord 6. The power cord 6 is connected to a power source 8. The power source may be a source of A/C current, as shown for example in FIG. 1, or alternatively, the power source 8 can also be a source of DC current. The device 2 can also include options for both A/C and DC current use. If A/C current is used a transformer (not shown) is used to convert A/C to DC current.

The electronic control unit 4 includes a display 10 preferably on a surface thereof. The display 10 can be a LCD screen or the like which is capable of displaying numbers and letters. Preferably the display 10 includes a portion for displaying the date 12, the time 14, a countdown number 16 indicating the number of doses remaining in the cartridge 70, the drug name or identification 18 contained within the cartridge 70, and an alarm indicator 20. Other items can also be displayed such as the expiration date of the drug within the cartridge 70, the dosage, the particle size, and the like (not shown).

The electronic control unit 4 preferably includes a speaker 22 housed within the electronic control unit 4 that is used to produce a sound alarm when one or more conditions are met. For example, the speaker 22 and the alarm indicator 20 might be triggered when the number of remaining doses falls below a pre-set number. As another example, the speaker 22 and alarm indicator might be triggered when the drug expiration date is near or has been surpassed. These features are preferably programmed into the electronic control unit 4 or cartridge 70.

The device 2 also includes in the electronic control unit 4 an on/off switch 24, a cancel switch 26, a prime pump switch 28, and a print/send switch 30. These switches 24, 26, 28, and 30 may take the form of a button or the like on the electronic control unit 4. Programming buttons 31 are also preferably provided on the electronic control unit 4. These programming buttons 31 can be used to change such things as the time and date displayed on the display 10. Preferably, these programming buttons 31 are recessed so they are not accidentally hit during use of the device 2.

Located in the electronic control unit 4 in the housing 5 is a communications port 32. The communications port 32 can include a modem jack, a USB port, a serial port, or a parallel port commonly found in personal computers. The communications port might also include an infrared LED or a radio frequency transmitter. The aforementioned are examples of the data transmission means used to transmit data from the device 2 to an external location or device. A cable 22 is connected from the electronic control unit 4 to the hand piece 50. The cable 22 includes one or more data transmission and power lines traveling between the hand piece 50 and the electronic control unit 4.

The hand piece 50 preferably includes a housing 52 shaped to contain the cartridge 70. At an end proximal to the cable 22, the hand piece 50 includes one or more electrical connectors 54 that are connected to the data and power lines within the cable 22. The electrical connectors 54 connect with corresponding electrical connectors (88, 90) on the cartridge 70. The electrical connectors 54 can include any number of commonly known components such as electrically conductive tabs, detents, projections, bumps, conductive springs, and the like. The housing 52 preferably includes one or more holes 56 therein to provide air to pass through during patient inhalation. The holes 56 might be eliminated entirely, however, if there is sufficient room for air to pass between the housing 52 and the cartridge 70.

Preferably, the hand piece 50 includes an inhalation sensor 58 that detects the onset of inhalation. The inhalation sensor 58 is connected to a data line 60 that passes to an electrical connector 54 or the like. The inhalation sensor 58 reports the inhalation data to the controller 150. Of course, the inhalation sensor 58 can instead be located within the cartridge 70.

Still referring to FIG. 1, the cartridge 70 includes a body portion 72. The body portion 72 is preferably shaped to closely fit within the hand piece 50. In this regard, a hand-in-glove type of arrangement is made between the cartridge 70 and the hand piece 50. The cartridge 70 can be removably engaged with the hand piece 50. The cartridge 70 can include an optional mouthpiece portion 73. The mouthpiece 73 might be permanently affixed to the cartridge 70, or alternatively, the mouthpiece 73 might be detachable from the cartridge 70. The cartridge 70 includes a drug storage container 74 that contains the drug 75. The drug storage container 74 acts a reservoir since the drug 75 contained within the container 74 is preferably in liquid form. Preferably, the cartridge 70 is disposable after use.

The cartridge 70 also includes an information storage element 76. The information storage element 76 stores data relating to the drug 75 within the cartridge 70 as well as information relating to the dosage and delivery of the drug 75, i.e., drug delivery protocol. The information storage device 76 can include a programmable chip, such as that shown in FIG. 1, or alternatively, the information storage element 76 may include a radio frequency tag 130, as shown in FIG. 3, or a bar code 140, as shown in FIG. 4. The information storage element 76 may also comprise a magnetic strip. The information storage element 76 is preferably programmable. Data such as the identification of the drug, the drug expiration date, the prescribed dosage of the drug, the minimum allowable time between doses, and drug delivery protocol, etc. can be programmed into the information storage element 76. The data can be preprogrammed by the manufacturer, or alternatively, by a health professional such as a doctor or pharmacist. The data stored within the information storage element 76 can be tailored to a particular drug 75 as well as to the particular patient.

Still referring to FIG. 1, one or more data transmission lines 86 are used to communicate the data stored on the information storage element 76 to one or more electrical connectors 88, 90 on the cartridge 70. These electrical connectors 88, 90 engage with corresponding electrical connectors 54 in the hand piece 50. A pump 92 is located in or adjacent to the drug storage container 74. The pump 92 is preferably a piezoelectric-driven pump 92 that is powered via power line 84. The power line 84 terminates in an electrical connector 98 to provide communication with the a electrical connector 54 in the hand piece 50 that is coupled to a source of power.

The drug 75 is pumped from the drug storage container 74 into a conduit 94. The conduit 94 provides a passageway for the drug 75 from the drug storage container 74 to a nebulizer element 100. The nebulizer element 100 creates a fine mist or cloud that includes small droplets of the drug 75. By forming small droplets of the drug 75 by use of the nebulizer element 100, the drug 75 is able to penetrate deep within the lungs with minimal loss of the drug 75 from adhesion to the cartridge 70 or to the back of the throat of the patient. The nebulizer element 100 can include any number of known devices used to generate a mist or cloud of drug 75. For example, the nebulizer element 100 may include a piezoelectric vibratory element, an ultrasonic generator, a nozzle, a pneumatic-based element and the like.

U.S. Pat. No. 5,813,614 discloses an example of a preferred nebulizer element 100. The '614 patent is incorporated by reference as if set forth fully herein. The nebulizer element 100 is an electrohydrodynamic nozzle 110.

Figure 2:
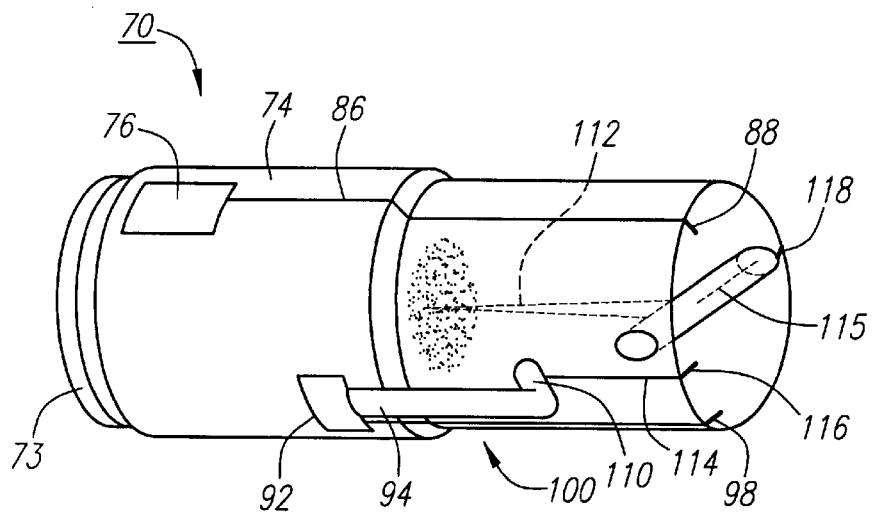
FIG. 2 illustrates one embodiment of the cartridge.
Figure 5:
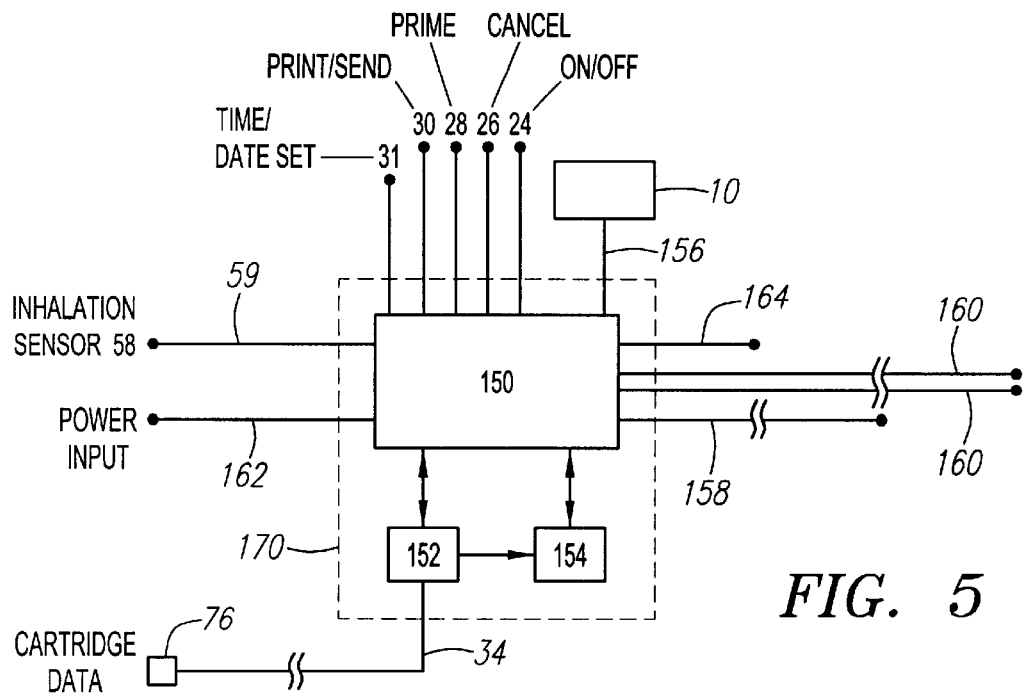
FIG. 5 illustrates a schematic representation of the control unit.

FIG. 2 illustrates one preferred embodiment of the nozzle 110. The nozzle 110 aims inside the cartridge 70 that delivers the liquid drug 75 into the lumen of the cartridge 70. Additional nozzles 110 (not shown) can also be located on the cartridge 70. A discharge electrode 112 is also located within the lumen of the cartridge 70. The nozzle 110 is preferably a high voltage nozzle 110 that imparts a negative charge to the drug 75 that is pumped out of the nozzle 110. The nozzle 110 is preferably connected via a power line 114 to a source of high voltage direct current via an electrical connector 116. The electrical connector 116 engages with a power electrical connector 54 in the hand piece 50. The negative charge imparted to the drug 75 droplets counterbalances the effects of surface tension, thereby permitting the formation of extremely small drug 75 droplets. The discharge electrode 112 preferably has a positive charge that is formed by connecting the discharge electrode 112 to a DC high voltage source via a power line 115 and electrical connector 118. The DC positive and negative voltages are produced by conventional circuitry that is controlled preferably by controller 150. The discharge electrode 112, with its positive charge, ionizes adjacent gas molecules and neutralizes the negative charge on. the aerosolized drug 75. The discharge electrode 112 also tends to pull the aerosol droplets away from the nozzle 110, thereby avoiding the buildup of condensed aerosol droplets on the nozzle 110.

FIG. 3 illustrates a embodiment of the invention wherein the information storage element 76 is a radio frequency (RF) tag 130. The RF tag 130 is affixed to the cartridge 70. A RF tag receiver 132 is affixed to the hand piece 50 and is used to pickup the information stored on the RF tag 130 and send the data via data line 134 to an electrical connector 54. This information is in turn reported to the electronic control unit 4. Preferably, the RF tag 130 is programmable.

FIG. 4 illustrates another embodiment of the invention wherein the information storage element 76 is a bar code 140. The bar code 140 is affixed to the cartridge 70. A bar code reader 142 is affixed to the hand piece 50 and is used to pickup the information stored on the bar code 140 and send the data via data line 144 to an electrical connector 54. This information is in turn reported to the electronic control unit 4. The bar code 140 is preferably programmable in the sense that the manufacturer or health care provider can affix a pre-programmed bar code 140 onto the cartridge 70.

FIG. 5 illustrates the controller 150, the cartridge reader 152, and the dosage storage element 154. The controller 150 is preferably a microprocessor that controls the operation of the device 2. The controller 150 receives signals from the on/off switch 24, the cancel switch 26, the prime pump switch 28, the print/send switch 30, and the program buttons 31 via respective signal lines. The inhalation sensor 58 also inputs a signal via signal line 59 to the controller 150. When inhalation is detected, signals are output from the controller 150 via signal line 156 to control the display 10 and the pump 92. The high voltages for the nozzle 110 and the discharge electrode 112 are powered via power lines 160. The cartridge reader 152 receives and stores the data from information storage element 76 transmitted via data lines within the cable 34. The cartridge reader 152 can comprise a microprocessor, memory, or the like. The cartridge reader 152 preferably reports the data contained within the information storage element 76 to the controller 150. Information such as the name of the drug, the expiration date, the dosage, the time between dosages, and the delivery protocol, etc. are stored within the electronic control unit 4.

The controller 150 is associated with a dosage storage element 154. The dosage storage element 154 contains information pertaining to the number of doses remaining for an individual cartridge 70. The dosage storage element 154 is a non-volatile memory which can include a bubble memory, microprocessor based circuit, memory chip, or the like. Preferably, each cartridge 70 has an individual unique cartridge identifier that is stored within the information storage element 76 and reported to the cartridge reader 152. The dosage storage element 154 preferably can associate a particular cartridge 70 with the number of remaining doses. This can be done even though the device 2 is turned off or the cartridge 70 is removed from the hand piece. When the inhalation sensor 58 detects the onset of inhalation, the controller starts the pump 92 to deliver the drug 75 to the nebulizer element 100. Since the patient has taken a dosage of the drug 75, the controller 150 reports this information to the dosage element 154, which stores the new number of doses remaining.

The controller 150, the cartridge reader 152, and the dosage element 154 can be individual units, as shown for example in FIG. 5, or alternatively, be incorporated into a single control unit as shown in outline 170. Control signals are transmitted to the pump 92 via pump control line 158. Power to the controller 150 is delivered via power line 162. A transmission line 164 transmits data to the communications device or communications port 32. The actual communication device, whether it is a modem, network card, RF transmitter, or the like, can be part of the control unit 150, or alternatively, separate from the control unit 150 and controlled via signals send via transmission line 164.

During operation of the device 2, the patient or health care provider turns on the device 2 via the on/off button 24. At this point the controller 150 senses that there is no cartridge 70 in the hand piece 50. The controller 150 sends a signal to the display 10 to display a message or indicator that the device 2 is ready for loading. The patient or other person then loads a cartridge 70 into the hand piece 50. The cartridge 70 is pushed into the housing 52 such that electrical connections are made between the cartridge 70 and the electrical connectors 54. Information stored within the information storage element 76 is then read by the cartridge reader 152. The cartridge reader 152 reads the unique identifier of the cartridge 70, the drug 75 name, the dosage information, the expiration date, the minimum time between doses, the drug delivery protocol, and any other information stored in the information storage element 76. The dosage storage element 154 is loaded with information pertaining to the number or remaining doses. If the cartridge 70 has never been used before, then the dosage storage element 154 is initialized with the total number of doses in the cartridge 70. If the cartridge 70 has already been used, the dosage storage element 154 recalls the number of doses remaining through the use of the unique cartridge identifier.

As an alternative to the unique cartridge identifier, the information storage element 76 located in the cartridge 70 can itself contain a countdown element to determine the number of doses remaining. In this case, the unique cartridge identifier may be eliminated entirely.

Once, loaded, the display preferably displays the number of doses remaining, the drug name, the date, and the time. The dosage storage element 154 also contains information indicating the last time the cartridge 70 was used. The dosage storage element 154 compares this time with the minimum time between doses for the particular drug. If the time interval is too small, the controller 150 will not let the pump 92 operate. Preferably, if the time interval is too small, the controller 150 also signals the display 10 to issue an alarm 20. The speaker 22 may also notify the patient that not enough time has elapsed.

Once the container 70 is properly loaded and the minimum time between doses has elapsed, the drug can be delivered to the patient. The pump 92 can be primed by depressing the prime pump switch 28. This might be needed, for example, on the first Use of a new cartridge 70. On inhalation, the inhalation sensor 58 signals the controller 150 to pump the drug 75 via the pump 92. The drug 75 delivered to the nebulizer element 100 where the liquid is converted to a cloud or mist of droplets for inhalation. Inhalation of the drug 75 may occur over a rather short time frame, preferably under a minute or so. This is significantly shorter than prior art nebulizers that can take around ten to fifteen minutes to deliver the drug to the patient. It should be understood, however, that a particular drug delivery protocol may require the drug 75 to be delivered over a longer period of time. This information is preferably stored in the information storage element 76 of the cartridge 70.

In the embodiment with the nozzle 110, the controller 150 also controls the charge of the nozzle 110 and the charge on the discharge electrode 112. Minute charged droplets are formed containing a negative charge. These droplets are then attracted to and neutralized by the discharge electrode 112. The neutralized droplets then pass out of the cartridge 70 and into the patient's lungs.

An optional security feature can also be employed with the device 2. For example, each electronic control unit 2 may be initialized with a unique patient code. When the cartridges 70 are programmed by the manufacturer or health care provider, the information storage element 76 is also programmed with this patient identification code. During loading of the cartridge 70, the device 2 compares the code from the cartridge 70 with the code from the electronic control unit 4. If the patient identification codes from the cartridge 70 and the electronic control unit 2 do not match, then the device 2 will. not operate.

The present device can deliver any number of drugs 75 to a patient. For example, in addition to drugs 75 for the treatment of lung diseases such as asthma, the device 2 can also deliver chemotherapeutics and chemopreventatives to prevent lung cancer. Other examples include anti-infective agents used to treat infection of the lungs. The device can also be used to deliver morphine or insulin to a patient. The device is also useful for the delivery of DNA, proteins, and peptides.

Figure 6:
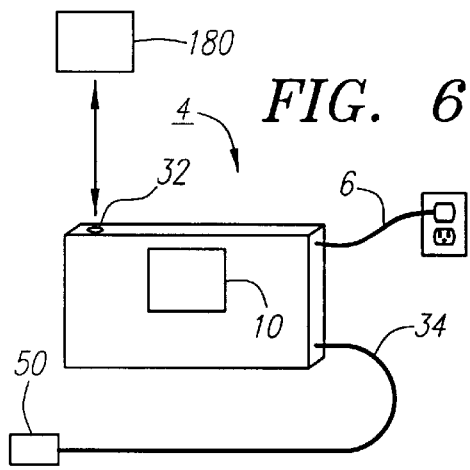
FIG. 6 illustrates the pulmonary delivery device transmitting data to a patient compliance output device.

The device 2, in another aspect of the invention, as seen in FIG. 6, transmits patient compliance information to a patient compliance output device 180. The patient compliance output device 180 can include, for example, a local printer, an offsite database accessible via a local area network (LAN) or a global communications network such as the Internet, a home base station, or a personal computer and the like.

The communications port 32, depending on its configuration, can transmit data to any number of patient compliance output devices 180. For example, a serial, parallel, or USB port may be connected via a cable to a local printer (not shown). A network card or a modem can be used to transmit data through a LAN or through the Internet. A RF transmitter or infrared LED can be used to transmit data to a nearby base station.

The information that is transmitted can include such things as the time, date, time between dosages, dosage delivered, etc. for each inhalation. This information can be delivered after each use of the device 2, or alternatively, at a pre-set time. For example, the device 2 can transmit data upon the switching of the print/send switch 30. Alternatively, the device 2 might transmit automatically at a pre-programmed time. For instance, the device 2 might be programmed to send data once a week or once a month. This information is used by the patient and/or health care provider to monitor patient compliance.

Figure 7:
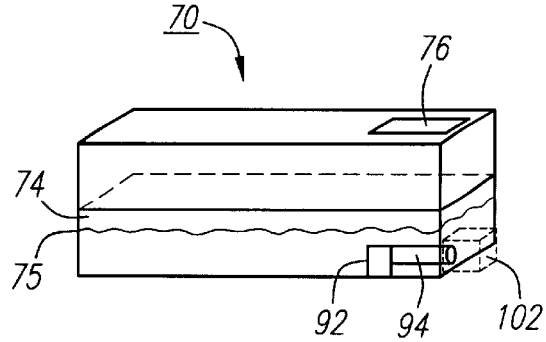
FIG. 7 is a schematic representation of the drug cartridge.

FIG. 7 illustrates a general schematic representation of a cartridge 70 including a drug storage container 74 having a drug 75 therein. A pump 92 is provided in the cartridge 70 to pump drug 75 into a conduit 94. The conduit 94 terminates to a head 102 which generates the mist or cloud of drug 75. The head 102, which can include the nebulizer element 100 can be found in the cartridge 70 or elsewhere such as in a hand piece 50 or the like (not shown). The cartridge 70 also includes an information storage element 76 that stores data relating to the drug 75, information relating to delivery of the drug 75, or information relating to the patient. The information storage element 76 is advantageously programmable. The information storage element 76 can include a programmable chip, RF transmitter, magnetic strip, bar code,or the like. The information or data stored in the information storage element 76 is read by reader which is preferably contained within a hand piece 50 or similar device.

The cartridge 70 is termed a "smart cartridge" in the sense that information pertaining to the drug 75, the delivery of the drug 75, and/or patient information is stored within the cartridge 70. A device with a reading mechanism can then access this information and control drug delivery 75 consistent with the data and/or instructions stored in the cartridge 70.

Figure 8:
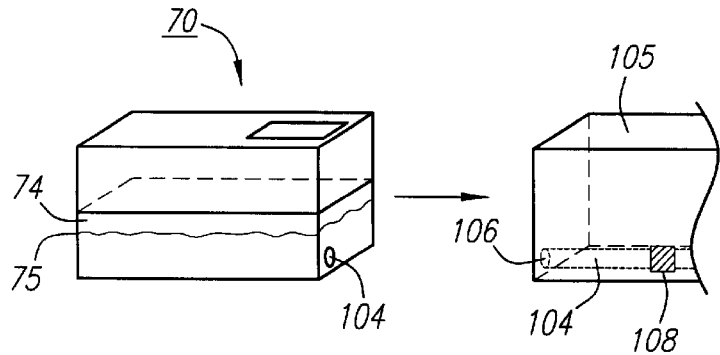
FIG. 8 is a schematic representation of another embodiment of the drug cartridge.

FIG. 8 illustrates another embodiment of the cartridge 70. In this embodiment, the cartridge 70 includes a drug storage container 74 containing the drug 75 and an information storage device 76. The information storage device 76 is preferably programmable. A port 104 is located in the drug storage container 74 and includes a hollow passageway that is in fluidic communication with the drug storage container 74. The port 104 can be a male-type port 104 as shown in FIG. 8, or alternatively, the port 104 can be a female-type port 104. During operation, the cartridge 70 is inserted into a device 105 wherein the port 104 engages with a corresponding port 106 in the device 105. The port 106 is connected to a conduit 107. The conduit 107 then leads to a pump 108 that delivers the drug 75 to a head 102 or nebulizer element 100 (not shown in FIG. 8).

In another aspect of the invention, information such as the number of doses remaining, the date and time of the last dose, and drug delivery protocol information can be re-written and stored within the information storage element 76 in the cartridge 70. This feature is useful when a patient might have multiple electronic control units 4. For example, a patient might have a device 2 for home use and a separate device 2 at work or at school. The patient might use the home device 2 in the morning and the non-home device 2 in the afternoon. The patient would use the same cartridge 70 for each device 2. By writing information to the information storage element 76 on the cartridge 70, the cartridge 70 can effectively be used on different devices 2. For example, if a patient tried to use the cartridge 70 on his or her device 2 at work soon after using the same cartridge 70 at the home device 2, the device 2 at work can recognize that not enough time has elapsed between doses. The work device 2 will not deliver the drug 75 until enough time has passed. Similarly, if a patient used the tenth remaining dose at his or her home device 2 and then another dose later in the day on the same cartridge 70 with the work device 2, the number of remaining doses (eight) would be stored within the cartridge 70. When the cartridge 70 is later used with the home device 2, the home device 2 reads that eight doses are remaining the cartridge 70. In this embodiment the information storage element 76 has read-write capabilities. The information storage element 76 can comprise a read write memory, and preferably, non-volatile memory which can include a memory chip, bubble memory, or the like. The information storage element 76 can also include a bi-directional RF tab, or read-writeable magnetic strip.

While embodiments of the present invention have been shown and described, various modifications may be made without departing from the scope of the present invention. For example, the nebulizer element 100 may be positioned external to the cartridge 70 such as in the hand piece 50. In addition, the pump 92 might be placed external to the cartridge 70. The invention, therefore, should not be limited, except to the following claims, and their equivalents.

What is claimed is:

1. A pulmonary drug delivery device comprising:
   an electronic control unit, said electronic control unit including:
      a controller;
      a cartridge reader;
      a display;
   a hand piece connected to said electronic control unit via a cable;
   a cartridge having a lumen therethrough, the cartridge being detachably engaged with said hand piece, said cartridge including a drug storage container including a drug stored therein, an electrically chargeable nozzle and a discharge electrode disposed within the lumen of the cartridge, a pump for pumping the drug out of the electrically chargeable nozzle, and an information storage element disposed on the cartridge;
   wherein the controller controls the pump and the charge of the nozzle and the charge on the discharge electrode in accordance with instructions stored in the information storage element.

2. A pulmonary drug delivery device according to claim 1, said electronic control unit further comprising a dosage storage element.

3. A pulmonary drug delivery device according to claim 2, said dosage storage element storing the number or remaining doses for said cartridge.

4. A pulmonary drug delivery device according to claim 3, said electronic control unit further comprising data transmission means.

5. A pulmonary drug delivery device according to claim 1, said electronic control unit further comprising an alarm.

6. A pulmonary drug delivery device according to claim 1, said hand piece further comprising an inhalation sensor.

7. A pulmonary drug delivery device according to claim 2, the dosage storage element comprises a memory.

8. A pulmonary drug delivery device according to claim 1, wherein the information storage element is programmable.

9. A pulmonary drug delivery device according to claim 8, the information storage element comprises a programmable memory.

10. A pulmonary drug delivery device according to claim 8, the information storage element comprises an RF tag.

11. A pulmonary drug delivery device according to claim 8, the information storage element comprises a bar code.

12. A pulmonary drug delivery device according to claim 8, wherein the information storage element also stores drug identification information.

13. A pulmonary drug delivery device according to claim 8, wherein the information storage element also stores drug delivery protocol.

14. A pulmonary drug delivery device according to claim 8, wherein the information storage element also stores the minimum time between dosages.

15. A pulmonary drug delivery device according to claim 1, wherein said cartridge contains a plurality of doses.

16. A pulmonary drug delivery device according to claim 1, wherein said display displays the number of remaining dosages.

17. A pulmonary drug delivery device for delivering a drug to a patient comprising:
   an electronic control unit, said electronic control unit including:
      a controller;
      a cartridge reader;
      a dosage storage element;
      a display;
   a hand piece connected to said electronic control unit via a cable; and
   a cartridge having a lumen therethrough, the cartridge being detachably engaged with said hand piece, said cartridge including a drug storage container including a drug stored therein, an electrically chargeable nozzle and a discharge electrode disposed within the lumen of the cartridge, a pump for pumping the drug out of the electrically chargeable nozzle, and an information storage element disposed on the cartridge;
   wherein the controller controls the pump and the charge of the nozzle and the charge on the discharge electrode in accordance with instructions stored in the information storage element.

18. A pulmonary drug delivery device for delivering a drug to a patient comprising:
   an electronic control unit, said electronic control unit including:
      a controller;
      a cartridge reader;
      a dosage storage element;
      data transmission means for transmitting patient compliance information to an output device;
      a display;
   a hand piece connected to said electronic control unit via a cable; and
   a cartridge having a lumen therethrough, the cartridge being detachably engaged with said hand piece, said cartridge including a drug storage container including a drug therein, an electrically chargeable nozzle and a discharge electrode disposed within the lumen of the cartridge, a pump for pumping the drug out of the electrically chargeable nozzle, and an information storage element disposed on the cartridge;
   wherein the controller controls the pump and the charge of the nozzle and the charge on the discharge electrode in accordance with instructions stored in the information storage element.

19. A pulmonary drug delivery device according to claim 18, said dosage storage element storing the number of remaining doses for said container.

20. A pulmonary drug delivery device according to claim 18, the dosage storage element comprises a memory.

21. A pulmonary drug delivery device according to claim 18, wherein the information storage element is programmable.

22. A pulmonary drug delivery device according to claim 21, the information storage element comprises a programmable memory.

23. A pulmonary drug delivery device according to claim 21, the information storage element comprises an RF tag.

24. A pulmonary drug delivery device according to claim 21, the information storage element comprises a bar code.

25. A cartridge for containing a drug comprising:

a lumen region inside the cartridge;

a drug storage container for storing the drug;

a pump disposed in the cartridge for pumping drug from the storage container to a conduit;

an electrically chargeable nozzle coupled to the conduit, the electrically chargeable nozzle disposed so as to aim inside the lumen;

a discharge electrode disposed within the lumen of the cartridge;

a programmable information storage element disposed on the cartridge, the programmable information storage element containing information regarding operation of the pump and information regarding electrical charges that are to be applied to the electrically chargeable nozzle and the discharge electrode using an external controller.

26. A cartridge according to claim 25, the information storage element comprises a programmable memory.

27. A cartridge according to claim 25, the information storage element comprises an RF tag.

28. A cartridge according to claim 25, the information storage element comprises a bar code.

29. A method of delivering a drug to a patient comprising the steps of:

providing an electronic control unit having a hand piece connected thereto;

providing a cartridge containing a drug therein, the cartridge further including a lumen therethrough, a drug storage container adapted to contain a drug therein, an electrically chargeable nozzle and a discharge electrode disposed within the lumen, a pump for pumping the drug out of the electrically chargeable nozzle, and an information storage element;

engaging the cartridge with the hand piece;

retrieving data stored in the information storage element and transmitting the data to the electronic control unit, the data including instructions for pumping the drug and charging the electrically chargeable nozzle and the discharge electrode; and delivering the drug to the patient in accordance with the data transmitted to the electronic control unit.

* * * * *